United States Patent
Cedarbaum et al.

(10) Patent No.: US 7,449,182 B2
(45) Date of Patent: Nov. 11, 2008

(54) THERAPEUTIC COMBINATION OF A VEGF ANTAGONIST AND ANTI-HYPERTENSIVE AGENT

(75) Inventors: Jesse M. Cedarbaum, Larchmont, NY (US); Jocelyn Holash, Alameda, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/002,115

(22) Filed: Dec. 14, 2007

(65) Prior Publication Data

US 2008/0145363 A1    Jun. 19, 2008

Related U.S. Application Data

(62) Division of application No. 11/350,145, filed on Feb. 8, 2006, now Pat. No. 7,354,581.

(60) Provisional application No. 60/652,394, filed on Feb. 11, 2005.

(51) Int. Cl.
*A61K 38/18* (2006.01)
*C07K 14/71* (2006.01)
*C12N 15/62* (2006.01)

(52) U.S. Cl. .................. 424/134.1; 424/192.1; 514/2; 514/12; 530/350; 536/23.4

(58) Field of Classification Search .............. None
See application file for complete search history.

(56) References Cited

U.S. PATENT DOCUMENTS 6,897,294 B2 * 5/2005 Davis-Smyth et al. ...... 530/350
2003/0144298 A1   7/2003 Curwen et al.

FOREIGN PATENT DOCUMENTS

WO    WO 2004/110490    12/2004
WO    WO 2005/000895    1/2005

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Disclosed are compositions and methods for treating a disease or condition related to angiogenesis with a vascular endothelial growth factor (VEGF) inhibitor and one or more anti-hypertensive agent(s). The method of the invention is useful for preventing the development of hypertension and/or reducing hypertension in a subject treated with a VEGF inhibitor.

5 Claims, No Drawings

SEQUENCE LISTING

<160> NUMBER OF SEQ ID NOS: 4

<210> SEQ ID NO 1
<211> LENGTH: 1453
<212> TYPE: DNA
<213> ORGANISM: Artificial Sequence
<220> FEATURE:
<223> OTHER INFORMATION: Synthetic

<400> SEQUENCE: 1

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaagtttc cacttgacac tttgatccct gatggaaaac      300
```

```
gcataatctg ggacagtaga aagggcttca tcatatcaaa tgcaacgtac aaagaaatag    360
ggcttctgac ctgtgaagca acagtcaatg gcatttgta  taagacaaac tatctcacac    420
atcgacaaac caatacaatc atagatgtgg ttctgagtcc gtctcatgga attgaactat    480
ctgttggaga aagcttgtc  ttaaattgta cagcaagaac tgaactaaat gtggggattg    540
acttcaactg gaataccct  tcttcgaagc atcagcataa gaaacttgta aaccgagacc    600 taaaaccca  gtctgggagt gagatgaaga aattttttgag caccttaact atagatggtg    660
taacccggag tgaccaagga ttgtacacct gtgcagcatc cagtgggctg atgaccaaga    720
agaacagcac atttgtcagg gtccatgaaa agggcccggg cgacaaaact cacacatgcc    780
caccgtgccc agcacctgaa ctcctggggg gaccgtcagt cttcctcttc cccccaaaac    840
ccaaggacac cctcatgatc tcccggaccc ctgaggtcac atgcgtggtg gtggacgtga    900
gccacgaaga ccctgaggtc aagttcaact ggtacgtgga cggcgtggag gtgcataatg    960
ccaagacaaa gccgcgggag gagcagtaca acagcacgta ccgtgtggtc agcgtcctca   1020
ccgtcctgca ccaggactgg ctgaatggca aggagtacaa gtgcaaggtc tccaacaaag   1080
ccctcccagc ccccatcgag aaaaccatct ccaaagccaa agggcagccc cgagaaccac   1140
aggtgtacac cctgccccca tcccgggatg agctgaccaa gaaccaggtc agcctgacct   1200
gcctggtcaa aggcttctat cccagcgaca tcgccgtgga gtgggagagc aatgggcagc   1260
cggagaacaa ctacaagacc acgcctcccg tgctggactc cgacggctcc ttcttcctct   1320
atagcaagct caccgtggac aagagcaggt ggcagcaggg gaacgtcttc tcatgctccg   1380
tgatgcatga ggctctgcac aaccactaca cgcagaagag cctctccctg tctccgggta   1440
aatgagcggc cgc                                                      1453
```

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
             20                  25                  30

Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
```

```
                145                 150                 155                 160
Trp Glu Tyr Pro Ser Ser Lys His Gln His Lys Lys Leu Val Asn Arg
                    165                 170                 175

Asp Leu Lys Thr Gln Ser Gly Ser Glu Met Lys Lys Phe Leu Ser Thr
                180                 185                 190

Leu Thr Ile Asp Gly Val Thr Arg Ser Asp Gln Gly Leu Tyr Thr Cys
            195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 3
<211> LENGTH: 1377
<212> TYPE: DNA
<213> ORGANISM: Artificial Sequence
<220> FEATURE:
<223> OTHER INFORMATION: Synthetic

<400> SEQUENCE: 3

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
```

-continued

```
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata agaaacttgt aaaccgagac     540
ctaaaaaccc agtctgggag tgagatgaag aaatttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga       1377

<210> SEQ ID NO 4
<211> LENGTH: 458
<212> TYPE: PRT
<213> ORGANISM: Artificial Sequence
<220> FEATURE:
<223> OTHER INFORMATION: Synthetic

<400> SEQUENCE: 4

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

-continued

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
        210                 215                 220

Phe Val Arg Val His Glu Lys Asp Lys Thr His Thr Cys Pro Pro Cys
225             230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```

THERAPEUTIC COMBINATION OF A VEGF ANTAGONIST AND ANTI-HYPERTENSIVE AGENT

CROSS-REFERENCE TO RELATED APPLICATIONS

This application is a divisional of U.S. patent application Ser. No. 11/350,145, filed 8 Feb. 2006, now U.S. Pat. No. 7,354,581, which claims the benefit under 35 USC § 119(e) of U.S. Provisional 60/652,394 filed 11 Feb. 2005, which application is herein specifically incorporated by reference in its entirety.

BACKGROUND

1. Field of the Invention

The field of the invention is related to therapeutic methods of treating diseases in a mammal with a vascular endothelial growth factor (VEGF) antagonist in combination with one or more anti-hypertensive agents.

2. Description of Related Art

Vascular endothelial growth factor (VEGF) has been recognized as a primary stimulus of angiogenesis in pathological conditions. Approaches to methods of blocking VEGF include soluble receptor constructs, antisense molecules, RNA aptamers, and antibodies. See, for example, PCT WO/0075319, for a description of VEGF-receptor based antagonists.

Combination therapies using an anti-VEGF antibody and chemotherapeutic agents, such as paclitaxel (TAXOL™), are known (see, for example, U.S. Pat. No. 6,342,219).

BRIEF SUMMARY OF THE INVENTION

In one aspect, the invention features a pharmaceutical composition comprising a high affinity vascular endothelial cell growth factor (VEGF) antagonist, one or more anti-hypertensive therapeutic agent(s), and a pharmaceutically acceptable carrier.

More specifically, the VEGF antagonist a high affinity fusion protein dimer (or "trap") comprising a fusion polypeptide having an immunoglobulin-like (Ig) domain 2 of the VEGF receptor Flt1 and Ig domain 3 of the VEGF receptor Flk1 or Flt4, and a multimerizing component. Even more specifically, the VEGF antagonist comprises a fusion polypeptide selected from the group consisting of Flt1D2.Flk1D3.FcΔC1(a) (SEQ ID NOs:1-2), VEGFR1R2-FcΔC1(a) (SEQ ID NOs:3-4), or a functionally equivalent thereof.

In specific embodiments, the one or more anti-hypertensive therapeutic agent are selected from the group consisting of ACE inhibitors (ACCUPRIL™ (Parke-Davis); ALTACE™ (Monarch); CAPTOPRIL™ (Mylan); ENALAPRILATE™ (Baxter); LOTENSIN™ (Novartis); MAVIK™ (Bristol-Myers Squibb); PRINIVIL™ (Merck); UNIVASC™ (Schwarz), VASOTEC™ (Merck); calcium-channel antagonists such as nifedipine, β-adrenergic receptor antagonists, such as for example, propanalol, sotalol; angiotensin II receptor antagonists; α-adrenergic receptor antagonists; direct active vasodilators; and diuretic agents used in the treatment of hypertension. In preferred embodiments, the anti-hypertensive therapeutic agent is an ACE inhibitor or a β-adrenergic receptor blocker.

In a second aspect, the invention features a pharmaceutical composition comprising a vascular endothelial cell growth factor (VEGF) antagonist, one or more anti-hypertensive therapeutic agent(s), and a pharmaceutically acceptable carrier, wherein the VEGF antagonist is a dimer composed of two fusion proteins each having an immunoglobulin-like (Ig) domain 2 of the VEGF receptor Flt1 and Ig domain 3 of the VEGF receptor Flk1 or Flt4, and a multimerizing component. In specific embodiments, the VEGF antagonist is selected from the group consisting of Flt1D2.Flk1D3.FcΔC1(a) (SEQ ID NOs:1-2), VEGFR1R2-FcΔC1(a) (SEQ ID NOs:3-4), or a functionally equivalent thereof.

In a third aspect, the invention features a method of treating a disease or condition which is ameliorated, inhibited, or reduced by a VEGF antagonist in a human, comprising administering a combination of a vascular endothelial growth factor (VEGF) antagonist and at least one anti-hypertensive agent.

The combined therapeutics of the invention achieves maximal anti-angiogenic activity while minimizing the known side effects resulting from treatment with anti-angiogenic agents, specifically, hypertension. The combination of an anti-angiogenic agent with an ACE inhibitor or angiotensin receptor blocker may also be used to prevent proteinuria in subjects at risk thereof.

Diseases and/or conditions, or recurrences thereof, which are ameliorated, inhibited, or reduced by treatment with the combination of the invention are those treated with a VEGF inhibitor such as the VEGF trap described above. For example, conditions ameliorated by treatment with a VEGF inhibitor include diseases such as cancer or diabetes. Conditions which are ameliorated, inhibited, prevented, or reduced by treatment with the combined therapeutics of the invention include vascular permeability, edema, or inflammation such as brain edema associated with injury, stroke, or tumor, edema associated with inflammatory disorders such as psoriasis or arthritis, asthma, edema associated with burns, ascites and pleural effusion associated with tumors, inflammation or trauma, chronic airway inflammation, capillary leak syndrome, sepsis kidney disease associated with increased leakage of protein, eye disorders such as eye related macular degeneration and diabetic retinopathy, abnormal angiogenesis such as polycystic ovary disease, entometriosis and endometrial carcinoma. A VEGF inhibitor may also be used to induce regression or reduction of the size of an existing tumor or metastatic cancer; diabetes, decrease tumor neovascularization, improve transplant corneal survival time, inhibit corneal transplant rejection or corneal lympangiogenesis and angiogenesis.

A subject to be treated is preferably a subject with one of the above listed conditions who suffers from hypertension, is at risk for development of hypertension or in which the prevention or inhibition of hypertension is desirable, e.g., a subject at risk for cardiovascular disease, a subject over 65 years of age, or a patient who cannot otherwise be treated with an appropriate dose of the VEGF antagonist without developing hypertension.

The VEGF inhibitor and anti-hypertensive agent may be administered simultaneously, separately or in combination, or sequentially over a relatively short period of time, e.g., within minutes, hours, or days.

In a fourth aspect, the invention features a method of preventing the development of hypertension during treatment with a vascular endothelial growth factor (VEGF) inhibitor in a patient at risk thereof, comprising administering a combination of a VEGF) antagonist and at least one anti-hypertensive agent.

In a fifth aspect, the invention features a method of treating hypertension during treatment with a vascular endothelial growth factor (VEGF) inhibitor in a patient at risk thereof, comprising administering a combination of a VEGF) antagonist and at least one anti-hypertensive agent.

Other objects and advantages will become apparent from a review of the ensuing detailed description.

DETAILED DESCRIPTION

Before the present methods and compositions are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

In the normal mammal, blood pressure is strictly controlled by a complex system of physiological factors. This is important for survival because high blood pressure (hypertension) can lead to a number of adverse medical events and conditions, such as, for example, stroke, acute coronary syndrome, myocardial infarction, and renal failure. Studies show that VEGF transiently dilates coronary arteries in vitro (Ku et. al. (1993) Am J Physiol 265:H585-H592) and to induce hypotension (Yang et. al. (1996) J Cardiovasc Pharmacol 27:838-844). Methods for treating eclampsia and preemclampsia are known (see, for example, US patent application publication 2003/0220262, WO 98/28006, WO 00/13703) is described a method for treating hypertension comprising administering to a patient an effective amount of an angiogenic factor such as VEGF, or an agonist thereof. US patent application publication 2003/0144298 shows that administration of high levels of a VEGF receptor tyrosine kinase inhibitor leads to a sustained increase in blood pressure in rats when administered chronically.

VEGF Antagonists and VEGF-Specific Fusion Polypeptide Traps

In a preferred embodiment, the VEGF antagonist is a dimeric fusion protein capable of binding VEGF with a high affinity composed of two receptor-Fc fusion protein consisting of the principal ligand-binding portions of the human VEGFR1 and VEGFR2 receptor extracellular domains fused to the Fc portion of human IgG1 (termed a "VEGF trap"). Specifically, the VEGF trap consists of Ig domain 2 from VEGFR1, which is fused to Ig domain 3 from VEGFR2, which in turn is fused to the Fc domain of IgG1 (SEQ ID NO:2).

In a preferred embodiment, an expression plasmid encoding the VEGF trap is transfected into CHO cells, which secrete VEGF trap into the culture medium. The resulting VEGF trap is a dimeric glycoprotein with a protein molecular weight of 97 kDa and contains ~15% glycosylation to give a total molecular weight of 115 kDa.

Since the VEGF trap binds its ligands using the binding domains of high-affinity receptors, it has a greater affinity for VEGF than do monoclonal antibodies. The VEGF trap binds VEGF-A ($K_D$=1.5 pM), PLGF1 ($K_D$=1.3 nM), and PLGF2 ($K_D$=50 pM); binding to other VEGF family members has not yet been fully characterized.

Anti-Hypertensive Therapeutic Agents

The invention may be practiced with a VEGF inhibitor, preferably a VEGF trap as described in U.S. Pat. No. 6,833,349, herein specifically incorporated by reference, and an agent which is capable of lowering blood pressure. Anti-hypertensive agents include calcium channel blockers, angiotensin converting enzyme inhibitors (ACE inhibitors), angiotensin II receptor antagonists (A-II antagonists), diuretics, β-adrenergic receptor blockers, vasodilators and α-adrenergic receptor blockers.

Calcium channel blockers include amlodipine; bepridil; clentiazem; diltiazem; fendiline; gallopamil; mibefradil; prenylamine; semotiadil; terodiline; verapamil; aranidipine; barnidipine; benidipine; cilnidipine; efonidipine; elgodipine; felodipine; isradipine; lacidipine; lercanidipine; manidipine; nicardipine; nifedipine; nilvadipine; nimodipine; nisoldipine; nitrendipine; cinnarizine; flunarizine; lidoflazine; lomerizine; bencyclane; etafenone; and perhexyline.

Angiotensin converting enzyme inhibitors (ACE-Inhibitors) include alacepril; benazepril; captopril; ceronapril; delapril; enalapril; fosinopril; imidapril; lisinopril; moveltipril; perindopril; quinapril; ramipril; spirapril; temocapril; and trandolapril.

Angiotensin-II receptor antagonists include, but are not limited to: candesartan (U.S. Pat. No. 5,196,444); eprosartan; irbesartan; losartan; and valsartan.

β-blockers include, but are not limited to: acebutolol; alprenolol; amosulalol; arotinolol; atenolol; befunolol; betaxolol; bevantolot; bisoprolol; bopindolol; bucumolol; bufetolol; bufuralol; bunitrolol; bupranolol; butidrine hydrochloride; butofilolol; carazolol; carteolol; carvedilol; celiprolol; cetamolol; cloranololdilevalol; epanolol; indenolol; labetalol; levobunolol; mepindolol; metipranolol; metoprolol; moprolol; nadolol; nadoxolol; nebivalol; nipradilol; oxprenolol; penbutolol; pindolol; practolol; pronethalol; propranolol; sotalol; sulfinalol; talinolol; tertatolol; tilisolol; timolol; toliprolol; and xibenolol.

α-blockers include, but are not limited to: amosulalol; arotinolol; dapiprazole; doxazosin; fenspiride; indoramin; labetolol, naftopidil; nicergoline; prazosin; tamsulosin; tolazoline; trimazosin; and yohimbine.

Vasodilators include cerebral vasodilators, coronary vasodilators and peripheral vasodilators. Cerebral vasodilators include bencyclane; cinnarizine; citicoline; cyclandelate; ciclonicate; diisopropylamine dichloroacetate; eburnamonine; fasudil; fenoxedil; flunarizine; ibudilast; ifenprodil; lomerizine; nafronyl; nicametate; nicergoline; nimodipine; papaverine; tinofedrine; vincamine; vinpocetine; and viquidil.

Coronary vasodilators include, but are not limited to: amotriphene; bendazol; benfurodil hemisuccinate; benziodarone; chloracizine; chromonar; clobenfural; clonitrate; cloricromen; dilazep; dipyridamole; droprenilamine; efloxate; erythrityl tetranitrate; etafenone; fendiline; floredil; ganglefene; hexestrol bis(β-diethylaminoethyl)ether; hexobendine; itramin tosylate; khellin; lidoflazine; mannitol hexanitrate; medibazine; nitroglycerin; pentaerythritol tetranitrate; pentrinitrol; perhexyline; pimefylline; prenylamine; propatyl nitrate; trapidil; tricromyl; trimetazidine; trolnitrate phosphate; visnadine.

Peripheral vasodilators include, but are not limited to: aluminium nicotinate; bamethan; bencyclane; betahistine; bradykinin; brovincamine; bufeniode; buflomedil; butalamine; cetiedil; ciclonicate; cinepazide; cinnarizine; cyclandelate; diisopropylamine dichloroacetate; eledoisin; fenoxedil; flunarizine; hepronicate; ifenprodil; iloprost; inositol niacinate; isoxsuprine; kallidin; kallikrein; moxisylyte; nafronyl; nicametate; nicergoline; nicofuranose; nylidrin; pentifylline; pentoxifylline; piribedil; prostaglandin $E_1$; suloctidil; tolazoline; and xanthinol niacinate.

Diuretic includes but is not limited to diuretic benzothiadiazine derivatives, diuretic organomercurials, diuretic purines, diuretic steroids, diuretic sulfonamide derivatives, diuretic uracils and other diuretics such as amanozine; amiloride; arbutin; chlorazanil; ethacrynic acid; etozolin; hydracarbazine; isosorbide; mannitol; metochalcone; muzolimine; perhexyline; ticrynafen; triamterene; and urea.

Treatment Population

A human subject preferably treated with the combined therapeutics described herein is a subject in which it is desirable to prevent or reduce one or more side effects resulting from treatment with an anti-angiogenic agent, such as hypertension, proteinuria. Particularly preferred subjects are those suffering from hypertension, over 65 years of age, or subjects in which reduction of or prevention of undesirable side effects allows a maximal dose of the anti-angiogenic agent to be used which otherwise could not be used without placing the subject at risk for an adverse medical event. Patients suffering from renal cell carcinoma, pancreatic carcinoma, advanced breast cancer, colorectal cancer, malignant mesothelioma, multiple myeloma, ovarian cancer, or melanoma may be treated with the combined therapeutics of the invention. Diseases and/or conditions, or recurrences thereof, which are ameliorated, inhibited, or reduced by treatment with the combined therapeutics of the invention cancer, diabetes, vascular permeability, edema, or inflammation such as brain edema associated with injury, stroke, or tumor, edema associated with inflammatory disorders such as psoriasis or arthritis, asthma, edema associated with burns, ascites and pleural effusion associated with tumors, inflammation or trauma, chronic airway inflammation, capillary leak syndrome, sepsis kidney disease associated with increased leakage of protein, eye disorders such as eye related macular degeneration and diabetic retinopathy, abnormal angiogenesis such as polycystic ovary disease, entometriosis and endometrial carcinoma. A VEGF inhibitor may also be used to induce regression or reduction of the size of an existing tumor or metastatic cancer; diabetes, decrease tumor neovascularization, improve transplant corneal survival time, inhibit corneal transplant rejection or corneal lympangiogenesis and angiogenesis.

Combination Therapies

In numerous embodiments, a VEGF antagonist may be administered in combination with one or more additional compounds or therapies, including a second VEGF antagonist molecule. Combination therapy includes administration of a single pharmaceutical dosage formulation which contains a VEGF antagonist and one or more additional agents; as well as administration of a VEGF antagonist and one or more additional agent(s) in its own separate pharmaceutical dosage formulation. For example, a VEGF antagonist and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine; retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Methods of Administration

The invention provides compositions and methods of treatment comprising a VEGF antagonist, such as a VEGF antagonist, and an anti-hypertensive agent. Various delivery systems are known and can be used to administer the composition of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, nonporous, or gelatinous material, including membranes, such as silastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and mucoadhesive.

Pharmaceutical Compositions

The present invention provides pharmaceutical compositions comprising a VEGF antagonist, an anti-hypertensive agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The composition of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the composition of the invention that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one VEGF antagonist and at least one anti-hypertensive agent, and wherein the packaging material comprises a label or package insert which indicates that the VEGF antagonist and anti-hypertensive agent can be used for treating cancer or reducing tumor growth.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Treatment of Malignant Pleural Effusion and Prevention of Hypertension

Adult patients with pathologic diagnosis of stage IIIB-IV NSCLC who are eligible for systemic chemotherapy, and also have an MPE which requires therapeutic drainage are eligible for inclusion in the study. Patients undergoing chemotherapy with another agent, or having prior chemotherapy with an inhibitor of VEGF, or active or untreated brain metastases are excluded. Treatment with VEGF antagonist (SEQ ID NO:4) is an intravenous dose of 300-5000 mg/kg and an anti-hypertensive agent such as an ACE inhibitor or β-adrenergic receptor blocker. The anti-hypertensive therapeutic agent may be given separately or in combination with the VEGF antagonist, prior to administration of the VEGF antagonist, simultaneously, or following administration of the VEGF antagonist.

Example 2

Treatment of Solid Tumor and Prevention of Hypertension

Patients with refractory solid tumors or non-Hodgkin's lymphoma receiving no concurrent treatment for their cancer are treated with the VEGF trap (SEQ ID NO:4) as follows. The dose levels range from 100 to 5000 mg/kg given subcutaneously. Each patient receives a single initial dose of the VEGF trap followed by weekly injections at the required dose level. Blood pressure is monitored and tumor burden is assessed at the beginning and end of the weekly dosing period; patients with stable disease, partial or complete responses may continue dosing for up to an additional 6 months in a continuation study.

What is claimed:

1. A method of treating a disease or condition which is ameliorated, inhibited, or reduced by a VEGF antagonist in a human subject, comprising administering a combination of a vascular endothelial growth factor (VEGF) antagonist and at least one anti-hypertensive agent wherein the VEGF antagonist is VEGFR1R2-FcΔC1 (a) (SEQ ID NO:4).

2. The method of claim 1, wherein the disease or condition treated is selected from the group consisting of cancer, diabetes, vascular permeability, edema, psoriasis, arthritis, asthma, ascites, pleural effusion, chronic airway inflammation, capillary leak syndrome, sepsis, an eye disorder, abnormal angiogenesis, metastatic cancer, corneal transplant rejection, corneal lympangiogenesis, and corneal angiogenesis.

3. The method of claim 1, wherein the human subject suffers from hypertension, is at risk for development of hypertension, is a subject in which the prevention or inhibition of hypertension is desirable.

4. The method of claim 3, wherein the subject is at risk for cardiovascular disease, is over 65 years of age, or cannot otherwise be treated with an appropriate dose of the VEGF antagonist without developing hypertension.

5. The method of claim 1, wherein the VEGF antagonist and anti-hypertensive agent are administered separately or together.

* * * * *